United States Patent
Stephenson et al.

(10) Patent No.: US 11,896,768 B2
(45) Date of Patent: Feb. 13, 2024

(54) DIFFUSER ARRANGEMENTS FOR A VENT OF A RESPIRATORY INTERFACE

(71) Applicant: FISHER & PAYKEL HEALTHCARE LIMITED, Auckland (NZ)

(72) Inventors: Matthew Roger Stephenson, Auckland (NZ); Toong Chuo Lim, Auckland (NZ); Thomas Mark Richardson, Auckland (NZ); Kyle Gregory Brown, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 426 days.

(21) Appl. No.: 17/061,494

(22) Filed: Oct. 1, 2020

(65) Prior Publication Data

US 2021/0016042 A1    Jan. 21, 2021

Related U.S. Application Data

(62) Division of application No. 15/309,397, filed as application No. PCT/IB2015/053359 on May 8, 2015, now Pat. No. 10,828,453.

(Continued)

(51) Int. Cl.
*A61M 16/08* (2006.01)
*A61M 16/06* (2006.01)

(52) U.S. Cl.
CPC ........ *A61M 16/0816* (2013.01); *A61M 16/06* (2013.01); *A61M 16/0683* (2013.01); *A61M 16/0866* (2014.02); *A61M 2202/0225* (2013.01); *A61M 2205/02* (2013.01); *A61M 2205/42* (2013.01); *A61M 2205/75* (2013.01)

(58) Field of Classification Search
CPC .............. A61M 16/06; A61M 16/0611; A61M 16/0616; A61M 16/0622; A61M 16/0683; A61M 16/08; A61M 16/0816; A61M 16/0825; A61M 16/0866; A61M 16/0875; A61M 16/208; A61M 2205/42;
(Continued)

(56) References Cited

U.S. PATENT DOCUMENTS 4,688,567 A     8/1987   Kikuchi et al.
7,958,889 B1    6/2011   Fernandez-DeCastro
(Continued)

FOREIGN PATENT DOCUMENTS

CN    204208153 U       3/2015
WO    WO-2014035261 A1 *  3/2014  ............ A61M 16/06

OTHER PUBLICATIONS

Written Opinion on the International Searching Authority, PCT App. PCT/IB2015/053359, dated Aug. 15, 2015, in 9 pages.

*Primary Examiner* — Joseph D. Boecker
(74) *Attorney, Agent, or Firm* — Knobbe, Martens, Olson & Bear, LLP

(57) ABSTRACT

A diffuser element for use over a vent opening of a breathing assistance apparatus. In some configurations, the diffuser element is formed by knitting or weaving one or more threads together into an interlocking pattern. In some configurations, the diffuser pad has a first surface and an opposing second surface and at least the first surface includes a surface texture. Arrangements for coupling the diffuser element to a structure that defines or carries the vent are also disclosed.

11 Claims, 11 Drawing Sheets

Related U.S. Application Data

(60) Provisional application No. 62/150,764, filed on Apr. 21, 2015, provisional application No. 61/991,302, filed on May 9, 2014.

(58) Field of Classification Search
CPC ...... A61M 2205/75; A61M 2202/0085; A62B 9/02; A62B 18/00; A62B 18/02
See application file for complete search history.

(56) References Cited

U.S. PATENT DOCUMENTS

| | | | |
|---|---|---|---|
| 8,353,293 B1 * | 1/2013 | Fuhrman | A61M 16/0816 128/204.18 |
| 2004/0094157 A1 | 5/2004 | Dantanarayana et al. | |
| 2006/0266365 A1 | 11/2006 | Stallard | |
| 2009/0044810 A1 | 2/2009 | Kwok et al. | |
| 2010/0154798 A1 | 6/2010 | Henry et al. | |
| 2013/0160769 A1 | 6/2013 | Ng et al. | |
| 2015/0083136 A1 * | 3/2015 | Grashow | A61M 16/0683 128/205.25 |
| 2015/0209541 A1 * | 7/2015 | Harwood | A61M 16/0816 128/205.25 |
| 2017/0050057 A1 | 2/2017 | Sabolis et al. | |
| 2018/0001120 A1 | 1/2018 | Virr et al. | |

\* cited by examiner

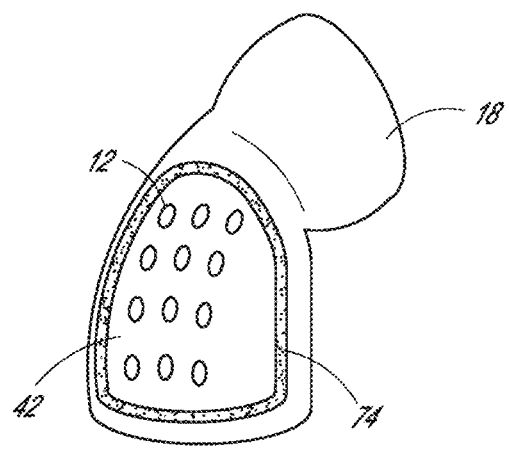
FIG. 19
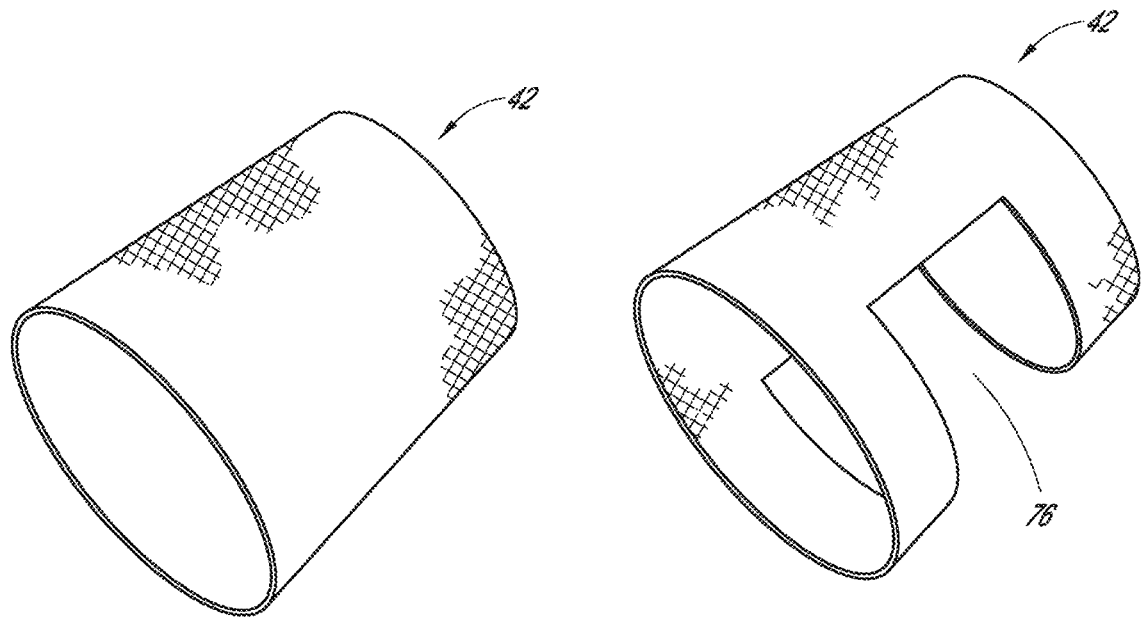
FIG. 20
FIG. 21

DIFFUSER ARRANGEMENTS FOR A VENT OF A RESPIRATORY INTERFACE

INCORPORATION BY REFERENCE TO ANY PRIORITY APPLICATIONS

The present application is a divisional application of U.S. patent application Ser. No. 15/309,397, filed on Nov. 7, 2016, which is a 371 of International PCT/IB2015/053359, filed on May 8, 2015, which claims priority benefit of U.S. Provisional Application Ser. No. 61/991,302, filed on May 9, 2014, and U.S. Provisional Application Ser. No. 62/150,764, filed on Apr. 21, 2015, the disclosures of each of which are hereby incorporated by reference in its entirety.

BACKGROUND

Field

The present disclosure generally relates to diffuser pads for bias gas flows. More particularly, the present disclosure relates to such diffuser pads having a woven or knitted configuration and/or arrangements for coupling a diffuser pad to an interface assembly or component thereof.

Description of Related Art

Sleep apnea generally is treated through the use of CPAP (continuous positive airway pressure) systems. In use, the CPAP system supplies a flow of pressurized breathing gases to a user through a patient interface, such as a mask. The mask or a component attached to or associated with the mask can include a vent to allow exhaled gases to be washed from within the mask.

Commonly, gases continually escape through the vent. In an attempt to quiet the flow of gases through the vent, various diffuser constructions have been used. In some configurations, the diffuser is simply an array of small holes. In some configurations, the diffuser is one or more flow passages that are covered with a diffuser mat.

SUMMARY

In some existing configurations, a connector (e.g., an elbow) that is used to connect a conduit to a mask includes an integrated vent. The vent includes one or more holes through which gas can escape to atmosphere from within the connector. The holes can be covered with a diffuser mat or pad. A cover can be used to secure the diffuser pad in position over the holes. Existing diffuser pads generally use matted fibres to diffuse the flow passing through the holes of the vent. The matted fibres are a non-woven material and the pad generally is formed of a non-woven polyester fibres. Some existing pads are constructed from a 12 mm thick white polyester material, which provides significant noise reduction and draft diffusion when compared to an array of holes without such a pad. Nevertheless, such pads provide some room for improvement.

For example, because the pads are formed of non-woven material, the pads do not offer strong bonding between the strands that make up the pad. Accordingly, during washing of the pads, the bonds may break down which can cause the pad to be difficult if not impossible to clean. Moreover, the loose, white polyester loops that define the non-woven material, readily trap dirt particles and become visually dirty very quickly.

Accordingly, an improved filter pad is desired that addresses one or more of these problems or that at least provides the public with a useful choice.

In some configurations, a diffuser pad has at least a portion formed of a knit or woven material.

In some configurations, a diffuser pad is formed from a plurality of threads. A first thread of said plurality of threads extends between a second thread and a third thread and the first thread is looped around at least a portion of the second thread and the third thread.

In some configurations, a diffuser pad has at least a portion formed of a knit or woven material with the diffuser pad comprising a first surface and a second surface. At least the first surface can be treated with a surface texture. In some such configurations, the first surface defines an inlet surface.

In some configurations, a woven or knitted diffuser pad can be arranged and configured to transmit a flow of between 16-22 L/min at 4 cm H2O, a flow of between 32-42 L/min at 13 cm H2O and a flow of between 43-59 L/min at 25 cm H2O.

In some configurations, a woven or knitted diffuser pad can be arranged and configured to transmit a flow of between 17-18 L/min at 4 cm H2O, a flow of between 33-35 L/min at 13 cm H2O and a flow of between 44-53 L/min at 25 cm H2O.

In some configurations, a diffuser arrangement for diffusing gases exhausted from a vent of a respiratory interface assembly includes a support structure comprising a first wall portion and a second wall portion defining a chamber therebetween. Each of the first wall portion and the second wall portion comprise perforations through which the exhaust gases can flow. A diffuser element is positioned within the chamber between the first wall portion and the second wall portion. The diffuser element is removable from the chamber or the support structure and the diffuser element are removable from a structure that defines or carries the vent.

In some configurations, the diffuser element is a relatively rigid disk. In some configurations, the disk is circular in shape.

In some configurations, an opening to the chamber is configured to allow the disk to be inserted into the chamber through the opening.

In some configurations, a hinge permits the first wall portion and the second wall portion to be separated to provide access to the chamber.

In some configurations, the diffuser element has at least a portion formed from a knit or woven material.

In some configurations, the diffuser element comprises a first surface and a second surface, and at least the first surface being treated with a surface texture.

In some configurations, the first surface defines an inlet surface and the surface texture comprises a roughened surface texture.

In some configurations, the diffuser element is arranged and configured to transmit a flow of between 16-22 L/min at 4 cm $H_2O$, a flow of between 32-42 min at 13 cm $H_2O$ and a flow of between 43-59 L/min at 25 cm $H_2O$.

In some configurations, the diffuser element is arranged and configured to transmit a flow of between 17-18 L/min at 4 cm $H_2O$, a flow of between 33-35 L/min at 13 cm $H_2O$ and a flow of between 44-53 L/min at 25 cm $H_2O$.

In some configurations, a diffuser arrangement for diffusing gases exhausted from a vent of a respiratory interface assembly includes a diffuser element having a body, wherein an entirety of the body is flexible such that the body of the diffuser element can conform to a shape of a structure that defines or carries the vent, wherein the body is sized and shaped to cover the vent.

In some configurations, the body of the diffuser element comprises mounting features at each end, the mounting features configured to allow the ends to be coupled to one another or to mounting elements of the structure that defines or carries the vent.

In some configurations, the body of the diffuser element is a strap and the mounting features comprise eyelets and the mounting elements comprise mounting posts, or vice-versa.

In some configurations, the body of the diffuser element is a strap and the mounting features comprise hooks and the mounting elements comprise mounting posts, or vice-versa.

In some configurations, the structure that defines or carries the vent is a mask frame, and the mounting elements are positioned on opposite sides of the vent.

In some configurations, the body of the diffuser element is a strap and the mounting features of the body comprise one eyelet and one mounting post.

In some configurations, the arrangement further comprises the structure that defines or carries the vent, the structure that defines or carries the vent is an elbow or other tubular member and the body of the diffuser element surrounds the elbow or other tubular member.

In some configurations, the body of the diffuser element is a sleeve.

In some configurations, the sleeve comprises at least a portion that is uninterrupted in a circumferential direction.

In some configurations, the sleeve is interrupted in a circumferential direction and includes end portions that are selectively coupled by a fastener. In some configurations, the fastener comprises at least one of a hook-and-loop or a magnetic fastener.

In some configurations, the sleeve comprises a window configured to engage an alignment feature of the structure that defines or carries the vent.

In some configurations, the arrangement further comprises the structure that defines or carries the vent and the alignment feature of the structure comprises a projection that extends in a circumferential direction.

In some configurations, the arrangement further comprises the structure that defines or carries the vent and the alignment feature of the structure comprises one or more hooks.

In some configurations, the body of the diffuser element comprises a peripheral mounting feature configured to engage a mounting element of a structure that defines or carries the vent.

In some configurations, the peripheral mounting feature comprises one of a cuff or a portion of a hook-and-loop fastener.

In some configurations, the body of the diffuser element is elastic.

In some configurations, the body of the diffuser element has at least a portion formed from a knit or woven material.

In some configurations, a diffuser arrangement for diffusing gases exhausted from a vent of a respiratory interface assembly includes a support structure comprising a perimeter portion and a plurality of interior supports. A diffuser element comprises a knit or woven structure in which one or more threads of the knit or woven structure wrap around one or both of the perimeter portion and at least one of the interior supports.

In some configurations, the interior supports comprise thread openings through which the threads of the knit or woven structure pass.

In some configurations, the support structure is configured to be connected to a structure that defines or carries the vent.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, one or more prior art publications may be referred to herein, this reference does not constitute an admission that any of these documents form part of the common general knowledge in the art in any country.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 19 is a perspective view of a conduit connector elbow and a diffuser element secured to the elbow by an edge mount arrangement.

FIG. 20 is a perspective view of a tube or sleeve type diffuser element configured for assembly onto a conduit connector elbow.

FIG. 21 is a perspective view of a partial tube or sleeve type diffuser element similar to the diffuser element of FIG. 20.

DETAILED DESCRIPTION

Figure 1:
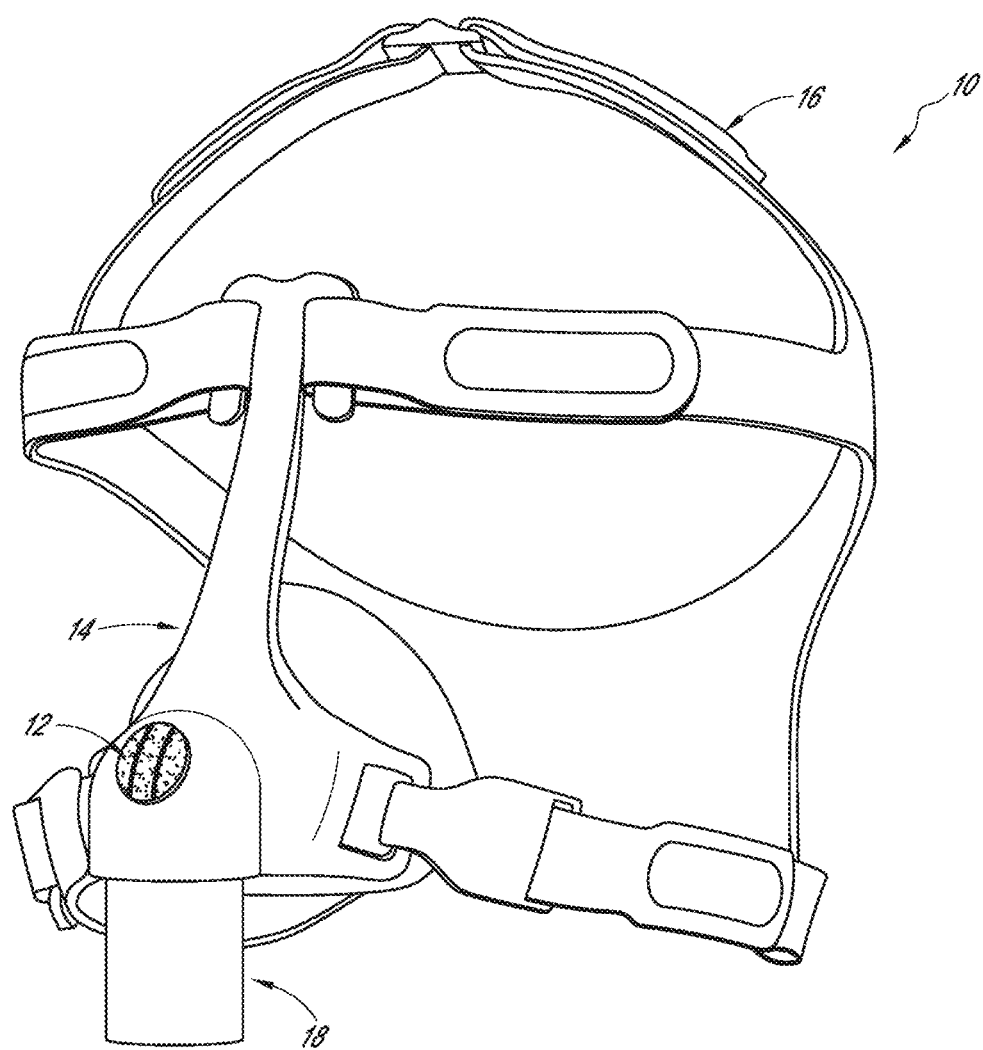
FIG. 1 is a perspective view of an interface assembly in the form of a nasal mask comprising a vent located on a body of the mask.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

With reference to FIG. 1, an interface assembly 10 for delivering a flow of breathing gas to a user or patient is illustrated. The interface assembly 10 comprises a mask 14 having a mask body, which carries a seal cushion that contacts and creates a seal with the face of the user. A retention arrangement, such as a headgear 16, is coupled to the mask 14 and engages the head of the user to retain the mask 14 in position on the user's face. A conduit connector, such as a conduit connector elbow 18, couples a gases conduit to the mask 14. The mask 14, the retention arrangement/headgear 16 and the conduit connector/elbow 18 can be of any suitable arrangement. For example, the mask 14 can comprise a single piece mask body or can comprise a multi-piece mask body. Such multi-piece mask bodies can comprise a seal housing that carries the seal cushion and a frame portion to which the headgear 16 connects. The seal housing and frame portion can be selectively coupled to one another, such as via a snap-fit arrangement or other removable coupling arrangement.

The interface assembly 10 comprises a vent 12 that communicates with an interior of the mask 14 and allows gases to be evacuated or washed from the interior of the interface assembly 10 to the surrounding atmosphere. The vent 12 can be of any suitable arrangement. For example, the vent 12 can include one or more holes through which gas can escape to surrounding atmosphere. In some configurations, the vent 12 is a bias flow vent comprising a plurality of relatively small holes or passages.

The vent 12 can be located at any suitable location on or near the interface assembly 10. In the interface assembly 10 of FIG. 1, the vent 12 is located on the conduit connector elbow 18. In some configurations, the vent 12 is located on the mask 14. In multi-piece mask bodies, the vent 12 can be located on either one or both of the seal housing and the frame portion. In other configurations, the vent 12 can be located on another component that forms a portion of, is related to, or is associated with the mask 14.

Figure 2:
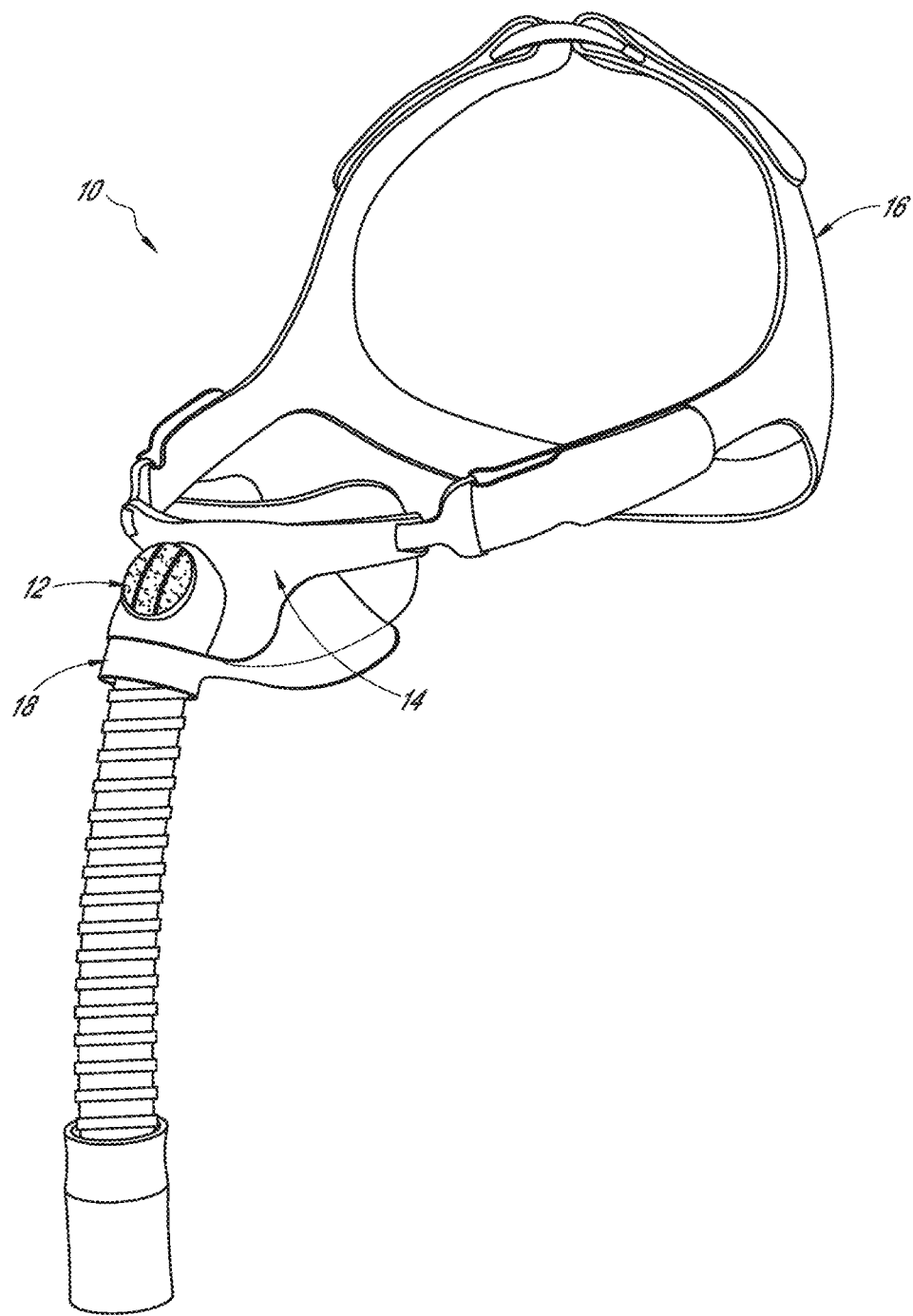
FIG. 2 is a perspective view of an interface assembly in the form of an under-nose mask comprising a vent located on a conduit connector elbow.

FIG. 2 illustrates another example of a patient interface 10. Similar to the interface 10 of FIG. 1, the interface 10 of FIG. 2 comprises a mask 14, a retention arrangement, such as a headgear 16, and a conduit connector, such as an elbow 18. The interface 10 of FIG. 2 comprises a mask in the form of an under-nose mask 14, in which the mask seal primarily engages the underside of the user's nose. The mask 14 can comprise a seal member carried by a mask body or frame. The interface 10 of FIG. 2 also comprises a vent 12, which can be provided at any suitable location. In the illustrated arrangement, the vent 12 is located on the conduit connector elbow 18. Although two examples of a patient interface 10 are shown in which the vent 12 is located on the elbow 18, the diffuser arrangements disclosed herein can be used in combination with other types of patient interfaces and other vent locations, including vents 12 located on the mask body, for example and without limitation.

Figure 3:
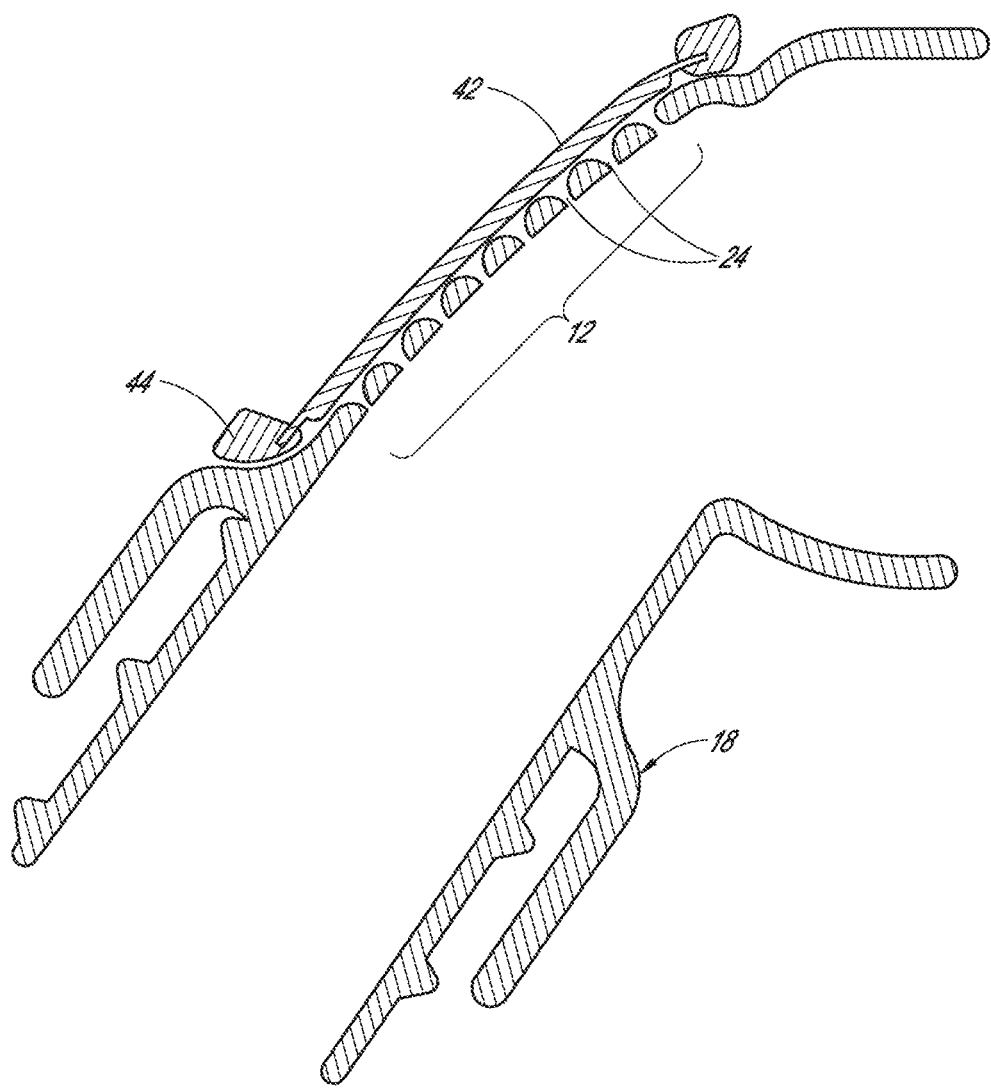
FIG. 3 is a sectioned view of a conduit connector elbow comprising a diffuser arrangement in combination with a vent.
Figure 4:
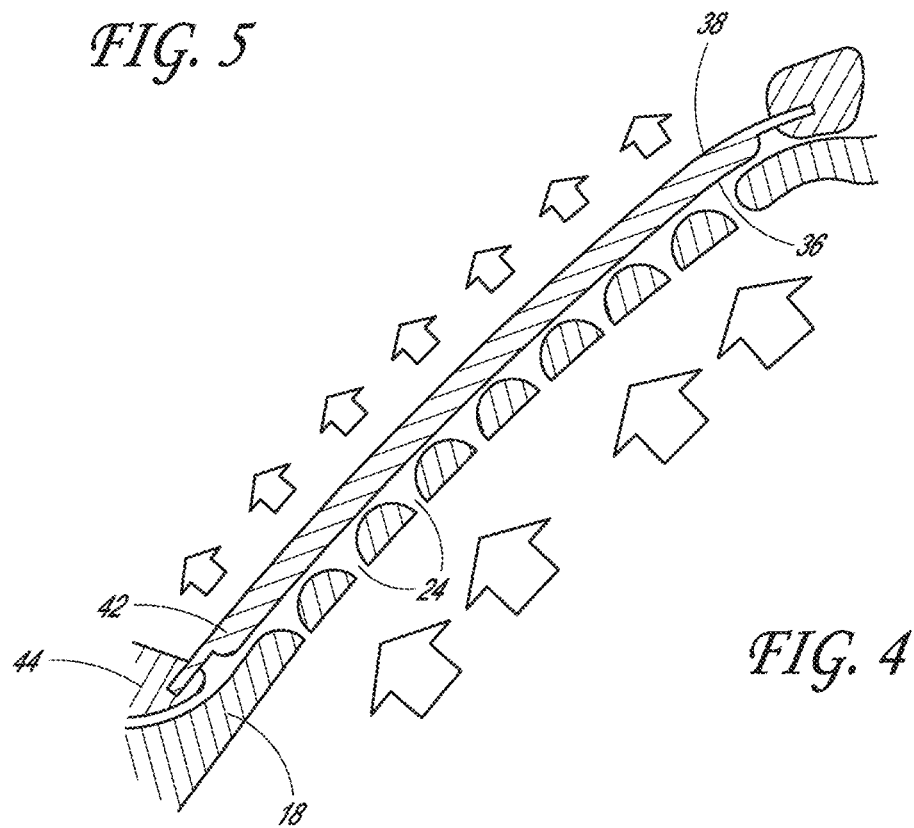
FIG. 4 is an enlarged sectioned view of the diffuser arrangement and vent of the elbow of FIG. 3.

With reference to FIGS. 3 and 4, a diffuser configuration is illustrated in combination with a vent 12 located on a portion or component of a patient interface assembly, such as a conduit connector elbow 18. Although the vent 12 is shown and described in connection with an elbow 18, the vent 12 can be located elsewhere on the patient interface 10 and any reference to the elbow 18 can also refer to other components in which the vent 12 can be located unless indicated otherwise either explicitly or by context. The elbow 18 includes one or more openings 24. The openings 24 can be configured in any suitable manner. For example, a cross-sectional size of the openings 24 can expand or contract or expand and contract depending upon the desired configuration. In some configurations, a cross-sectional size of some of the openings 24 can be configured to contract while others expand. In the illustrated configuration, a cross-sectional size of the openings 24 expand in an outward direction such that the flow of gases outward through the openings 24 can slow as the flow moves through the openings 24 as a result of the increasing cross-sectional area of the openings 24 in the flow direction.

A support structure, such as a frame 44, can be secured to the elbow 18 or other component in any suitable manner. In some configurations, the frame 44 is secured to the elbow 18 or other component in a removable manner, for example, by a snap-fit to the elbow 18 or other component. In other words, the frame 44 can be removed from the elbow 18 or other component for replacement or the like. In some configurations, the frame 44 is not necessarily designed for easy removal. Instead, in such configurations, a diffuser pad 42 is removably attached to the frame 44.

In the illustrated configuration, however, the diffuser pad 42 can be secured to the frame 44 such that the diffuser pad 42 is not easily removed from the frame 44, but the frame 44 is easily removed from the elbow 18 or other component. The diffuser pad 42 can be secured to the frame 44 in any suitable manner, such as molding, welding or adhesion. The frame 44 can help to maintain the location and the shape of the diffuser pad 42 relative to the openings 24. Other configurations are possible keeping in mind a desire to wash or otherwise clean the diffuser pad 42.

The frame 44 can be constructed from any suitable material or materials, including materials that are the same as or similar to the component or structure to which the frame 44 is attached. In some configurations, the frame 44 is constructed from polypropylene, nylon, polycarbonate or another similar material or combination of materials.

Figure 5:
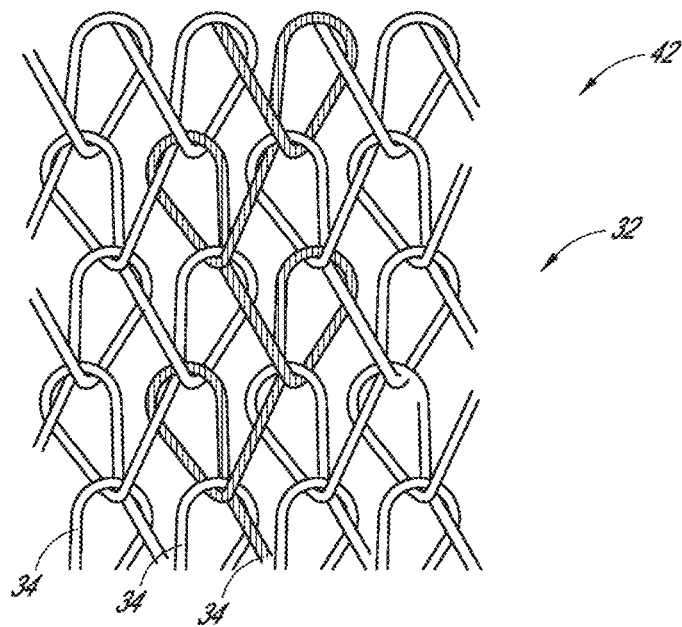
FIG. 5 is an enlarged, simplified view of a fabric useful as a diffuser pad.

With additional reference to FIG. 5, the diffuser pad 42 can be formed at least partially by a woven or knitted material 32. The material 32 can be woven or knit from one or more strands, threads 34 or the like. In the illustrated configuration, one thread 34 will interlock with two adjacent threads. In some configurations, as illustrated, the thread 34 interlocks with the adjacent thread on each side of the thread 34. Thus, the weaving or knitting process mechanically binds the fabric strands together.

The diffuser pad 42 can use any desired thread count, thread type, thread weight (i.e., thread diameter) or fabric geometry. By altering one or more of the thread count, thread type, thread weight, and fabric geometry, air flow through the diffuser pad 42 can be more accurately tailored. For example, the exhaust or bypass flow can be lower at lower mask pressures. For example, in some configurations, the diffuser pad 42 can be arranged and configured to transmit a flow of between 16-22 L/min at 4 cm H2O, a flow of between 32-42 L/min at 13 cm H2O and a flow of between 43-59 L/min at 25 cm H2O. In some such configurations, the diffuser pad 42 can be arranged and configured to transmit a flow of between 17-18 L/min at 4 cm H2O, a flow of between 33-35 L/min at 13 cm H2O and a flow of between 44-53 L/min at 25 cm H2O.

In some configurations, one or more diffuser pads 42 can be used to adjust the flow through the openings 24 simply by interchanging the diffuser pads 42 based upon the flow rating. In some configurations, one or more diffuser pads 42 can be stacked to alter the flow through the openings 24. In some configurations, the diffuser pad 42 can simply be designed to arrive at a desired flow through the openings 24. By altering the density of the fabric in any or all of the manners discussed above, a desired bypass or exhaust flow rate can be achieved. For example, reducing the density of the fabric can increase the bypass or exhaust flow rate through the openings 24. Accordingly, the diffuser pad 42 can have significantly improved durability while also providing the ability to more accurately tailor the airflow that is allowed to pass through the diffuser pad 42. Other configurations are also possible.

In addition to tailoring the density of the diffuser pad 42, different surface finishes can be provided to one or more regions of the diffuser pad 42. In some configurations, the entire exposed portion of the diffuser pad 42 can have the same surface finish. In some configurations, at least the portion of the diffuser pad 42 that will overlie the openings 24 can have the same surface finish. It has been discovered that characteristics of the flow through the vent 12 and/or diffuser pad 42 vary based upon the surface finish. For example, using roughened surface finishes (e.g., napping or sueding) is believed by the present inventors to help decelerate flow in a more gradual fashion, thereby further reducing, dampening or attenuating the noise associated with the bypass or exhaust flow relative to a similar material not having the roughened surface (e.g., a sheer finish).

In some configurations, both of the surfaces are textured. In some configurations, the diffuser pad 42 can have two different surface textures. In some such configurations, the surface with the relatively more rough texture can be positioned closer to the openings 24. In the illustrated configuration, a textured or roughened surface 36 can be placed towards the source of airflow (as indicated by the arrows). In some configurations, a non-textured or a sheer surface 38 can be placed away from the source of airflow. In other words, the textured surface 36 can be upstream of the non-textured surface 38. In addition to providing the benefit of better silenced bypass or exhaust flow, having the sheer surface 38 disposed toward the outside of the system can provide an improved appearance. A roughened surface finish can be a surface finish that has a greater roughness than another surface of the diffuser pad or a greater roughness than the relevant material or relevant portion of the material prior to treatment or other manipulation that increases its roughness. The roughened surface finish can be provided by the characteristics of the material itself (e.g., thread count, thread type, thread weight, fabric geometry, etc.), by manipulating the material to produce a roughened texture (e.g., napping or sueding), a combination of the foregoing or any other suitable process.

Although in some configurations the diffuser pad 42 is woven or knitted, other types of diffuser pads 42 can also be used in connection with the following diffuser arrangements. For example, the diffuser pads 42 can be constructed at least partially from a spacer fabric (a breathable neoprene alternative consisting of two covering fabrics connected with filaments in the middle), a microknit fabric, foam material or blow fibre material. Other suitable materials, including non-woven materials (e.g., matted fibres), can also be used.

Figure 6:
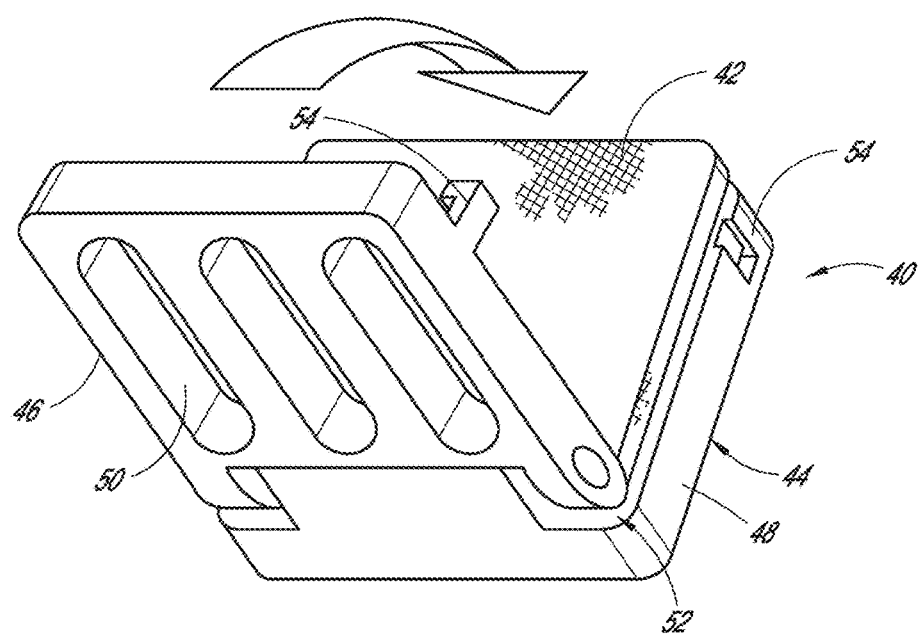
FIG. 6 is a perspective view of a diffuser pod assembly comprising a diffuser element and a support structure.

FIG. 6 illustrates a diffuser arrangement comprising a replaceable cartridge or pod 40 that can be removably coupled to an interface 10 or related component. The replaceable pod 40 can be coupled to the interface 10 or related component by any suitable arrangement, such as by a snap-fit arrangement, for example. The replaceable pod 40 can be positioned over the vent 12 of the interface 10 such that gases passing out of the vent 12 flow through the replaceable pod 40 in a manner suitable to diffuse the gases exiting the vent 12, similar to the arrangement illustrated in FIGS. 3 and 4. In some configurations, the replaceable pod 40 is removably coupled to a mask body of a mask 10, a conduit connector elbow 18 or another component or structure that defines or carries the vent 12.

In some configurations, the replaceable pod 40 comprises a diffuser element 42 and a support structure 44. The support structure 44 can be a relatively rigid structure, such as a frame or enclosure, constructed as least partially from a relatively rigid material, such as a plastic material. For example, the support structure 44 material can be the same as or similar to the material of the component or other structure to which the replaceable pod 40 is coupled. In some configurations, the support structure 44 is constructed from polypropylene, nylon, polycarbonate or another similar material or materials.

In some configurations, the support structure 44 comprises a first wall portion 46 and a second wall portion 48 that define a chamber or cavity therebetween. The diffuser element 42 is received within the chamber between the first wall 46 and the second wall 48 such that the diffuser element 42 is encapsulated within the support structure 44. One of the first wall portion 46 and the second wall portion 48 can be positioned adjacent to the vent 12 and the other of the first wall portion 46 and the second wall portion 48 can be downstream of the diffuser element 42 relative to the vent 12. The support structure 44 is perforated or otherwise configured to allow exhaust gases from the vent 12 to pass therethrough. In the illustrated arrangement, each of the first wall 46 and the second wall 48 comprises one or more openings 50 that allow exhaust gases to pass through the first wall 46, the diffuser element 42 and then through the second wall 48.

Such an arrangement facilitates the convenient replacement of the diffuser element 42. For example, the replaceable pod 40 can be removed from the component or other structure that defines the vent 12 for washing of the diffuser element 42. In some configurations, the diffuser element 42 can be cleaned while remaining encapsulated within the support structure 44. The presence of the support structure 44 can make it easier to hold and avoid damaging or losing the diffuser element 42. The replaceable pod 40 can be reattached to the vent 12 once the diffuser element 42 is dry. In some cases, multiple replaceable pods 40 can be available to the user (e.g., provided with the interface assembly 10) such that one pod 40 can be used while other pod(s) 40 are being cleaned or are in the process of drying.

As described above, in some configurations of the replaceable pod 40, the diffuser element 42 can be non-removably or permanently encapsulated within the support structure 44, such as during the manufacturing process and/or the first time the diffuser element 42 is loaded into the support structure 44. Such an arrangement could require replacement of the entire pod 40 at the end of the useful life of the diffuser element 42, but is advantageous in that the pod 40 is often larger, more rigid and easier to handle than the diffuser element 42 alone. In addition, the support structure 44 can protect the diffuser element 42 from damage.

However, in other configurations, it may be desirable for the replaceable pod 40 to be configured such that the diffuser element 42 is removable and/or replaceable. In the illustrated arrangement of FIG. 6, the support structure 44 can be opened to expose the chamber and the diffuser element 42. In particular, a hinge 52 can be provided between the first wall portion 46 and the second wall portion 48 such that the first wall portion 46 and the second wall portion 48 can be separated to allow access to the diffuser element 42 within the chamber of the support structure 44. In the illustrated arrangement, the hinge 52 is located at or near one end (e.g., the lower end) of the support structure 44. A releasable connector or coupling 54, such as a resilient snap or latch, can be spaced from the hinge 52 and configured to selectively secure the first wall portion 46 and the second wall portion 48 in a closed position.

In an alternative configuration, the second wall portion 48 can form a portion of the mask 14, elbow 18 or other component that defines or carries the vent 12 and the first wall portion 46 can be movably connected to the mask 14, elbow 18 or other component, such as via the hinge 52. In such configurations, the pod 40 can be integrated with the mask 14, elbow 18 or other component and may or may not be removable. Arrangements in which the diffuser element 42 is removable from the support structure 44 allows the diffuser element 42 to be cleaned or replaced without requiring replacement of the entire support structure 44. With such an arrangement, the diffuser element 42 can be routinely cleaned while in the support structure 44 and completely replaced on a periodic basis.

Figure 7:
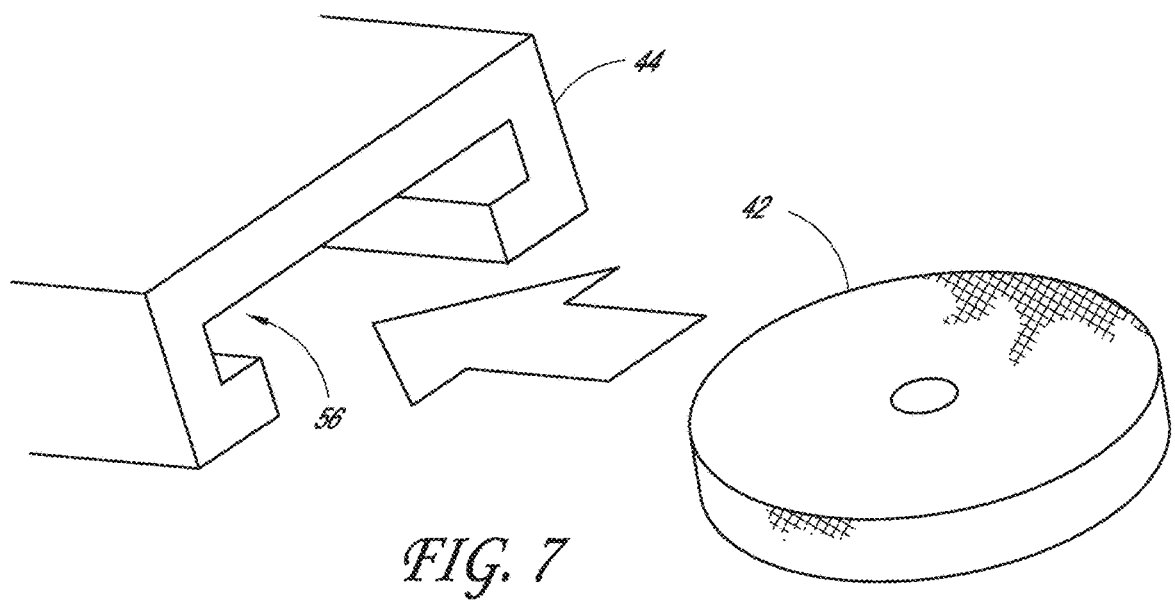
FIG. 7 is a perspective view of a diffuser assembly comprising a relatively rigid diffuser element and a receiving structure.

FIG. 7 illustrates a diffuser arrangement comprising a relatively rigid diffuser element 42 in the form of a disk. The diffuser disk 42 can be received within a chamber, cavity or slot 56 of a support structure 44, which places the diffuser disk 42 adjacent the vent 12. The diffuser disk 42 can be either upstream or downstream from the vent 12. In some configurations, the support structure 44 is integrated with the mask 14, elbow 18 or other component that defines or carries the vent 12. In such configurations, the slot 56 can be located behind or upstream from the vent 12 relative to a direction of exhaust gas flow. Alternatively, the diffuser disk 42 can be located downstream of the vent 12 and the support structure 44 can be perforated to allow relatively unimpeded flow compared to the vent 12, such as in a manner similar to the support structure 44 of FIG. 6. In other alternative configurations, the support structure 44 can be removable in a manner similar to the support structure 44 of FIG. 6, except the diffuser disk 42 is received in the slot 56 instead of being captured between a pair of hinged wall portions.

Preferably, the diffuser disk 42 is constructed to have enough rigidity to facilitate handling. In some configurations, the diffuser disk 42 is constructed with enough rigidity to allow insertion into and/or removal from the slot 56. The rigidity can be provided in any suitable manner. For example, rigidity can be provided by the selection of the material or manufacture characteristics of the diffuser disk 42, such as thread count, thread type, thread weight (i.e., thread diameter), fabric geometry or any other suitable characteristic, such as any of those discussed herein. In some configurations, rigidity can be provided by any suitable type of rigidizer, such as a frame or skeleton member, coating, integrated rigid element or integrated rigidized thread, for example and without limitation.

In some configurations, the diffuser disk 42 is circular in shape. Such an arrangement facilitates insertion into and removal from the slot 56. For example, the lack of corners inhibits or prevents the diffuser disk 42 from catching or snagging on any corners or edges of the support structure 44 that define or are located near the slot 56. In addition, the diffuser disk 42 does not need to be oriented in any particular manner relative to the slot 56 (with respect to rotation about a center of the circular disk 42). However, in other configurations, the diffuser disk 42 can comprise any other desired shape. Thus, as used herein, the term "disk" is not limited to circular shapes unless otherwise indicated.

Figure 8:
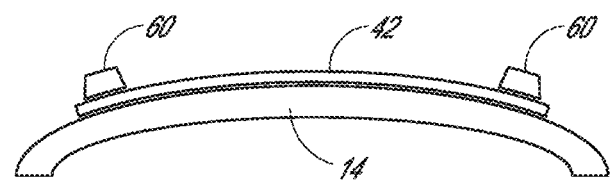
FIG. 8 illustrates a mask frame portion of an interface assembly and a diffuser element coupled to the mask frame via mounting posts or buttons.
Figure 9:
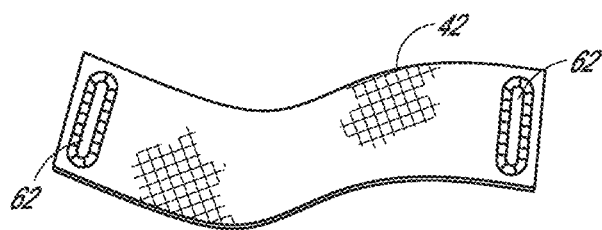
FIG. 9 illustrates the diffuser element of FIG. 8 separated from the mask frame.

FIGS. 8 and 9 illustrate another diffuser arrangement comprising a diffuser element 42 that is selectively connectable to the mask 14, elbow 18 or other component that defines or carries the vent 12. In the illustrated arrangement, the diffuser element 42 is in the form of a sheet or strap, which is attachable to a portion of the body or frame of the mask 14 that defines or carries the vent 12. In some configurations, the portion of the mask 14 defines a generally flat or slightly curved surface. That is, the portion of the mask 14 can be generally planar or can have a relatively large (continuous or variable) radius curvature. The mask 14 can comprise a pair of spaced apart mounting elements, such as mounting posts or buttons 60, configured to support the diffuser strap 42 adjacent the vent 12. In the illustrated arrangement, the mounting posts 60 include a shaft portion adjacent the body of the mask 14 and a larger diameter head portion positioned on the shaft opposite the body of the mask 14.

The diffuser strap 42 comprises a pair of eyelets 62 or other structures that define an opening configured to receive the mounting posts 60. With such an arrangement, the diffuser strap 42 can be assembled to and removed from the mounting posts 60 as desired. The mounting posts 60 can be spaced from one another on each side of the vent 12 a selected distance such that the diffuser strap 42 is held taut and preferably in contact with the body of the mask 14 to provide effective diffusion of the exhaust gases discharged from the vent 12.

In some configurations, at least a diffusing portion (portion positioned over the vent 12) of the diffuser strap 42 comprises a knitted or woven material, as described above. However, in other configurations, other suitable types of diffuser material can be used. In some configurations, the diffuser strap 42 is constructed substantially entirely from a diffuser material (with the possible exception of the eyelets 62 or other structures that define the openings). Accordingly, in some such configurations, the diffuser strap 42 does not include any rigid or hard portions or components such that the diffuser strap 42 is lighter and less bulky and is conformable to the shape of the surface against which the strap 42 is positioned in use. In some configurations, the diffuser strap 42 can be somewhat elastic in a lengthwise direction (between the eyelets 62) such that the strap 42 is stretched when assembled to the mounting post 60 to improve retention of the diffuser strap 42. Some stretch of the strap 42 can also improve conformance of the strap 42 with the surface against which it rests and can possibly reduce leakage between the mask 14 (or other component) and the diffuser strap 42.

Figure 10:
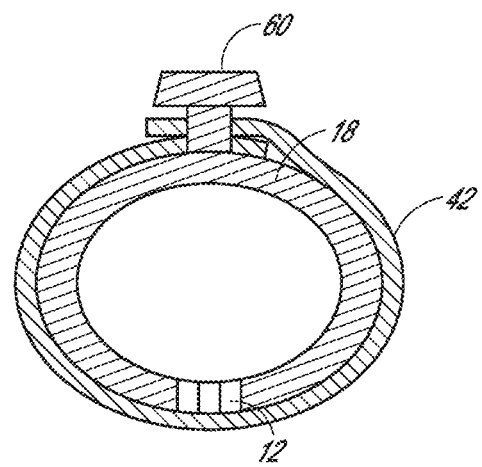
FIG. 10 is a sectional view of a conduit connector elbow incorporating a diffuser element and mounting arrangement similar to that of FIGS. 8 and 9.

FIG. 10 illustrates a diffuser arrangement comprising a diffuser element or strap 42 that is the same as or similar to the diffuser strap 42 of FIGS. 8 and 9. However, in the arrangement of FIG. 10, the vent 12 is defined or carried by the elbow 18 or another tubular component (e.g., a conduit) and the diffuser strap 42 is assembled to the elbow 18. In the illustrated arrangement, the diffuser strap 42 is wrapped around the elbow 18 over top of the vent 12. In some configurations, a single mounting post 60 is provided and the eyelet 62 of each end of the diffuser strap 42 is passed over the single mounting post 60.

In an alternative arrangement, the ends of the diffuser strap 42 can be coupled to one another and the strap 42 can be secured to the elbow 18 at least partially by a frictional force between the strap 42 and the elbow 18. If desired, additional support elements or surfaces (e.g., a shoulder or ledge) can be provided on the elbow 18 and contact the strap 42 to assist in keeping the strap 42 in place. Preferably, the diffuser strap 42 is taut or stretched when assembled. In some configurations, the mounting post 60 can be coupled to one end of the strap 42 and the eyelet 62 can be provided on the opposite end of the mounting post 60. The strap 42 can be wrapped around the elbow and the eyelet 62 can be passed over the mounting post 60 to secure the diffuser strap 42 to the elbow 18. The mounting post 60 can be secured to the strap 42 by any suitable arrangement, such as sewing, welding or over-molding, for example. In some configurations, the mounting post 60 can comprise a retention feature (e.g., flange or base) opposite the head portion and the mounting post 60 can be passed through an eyelet 62. In such an arrangement, eyelets 62 can be provided on each end of the strap 42.

Figure 11:
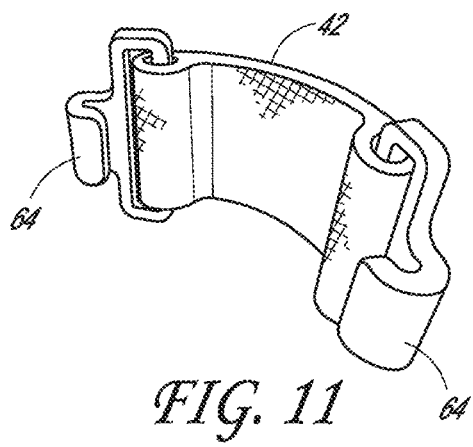
FIG. 11 illustrates a diffuser element comprising mounting elements, such as mounting hooks, on each end.
Figure 12:
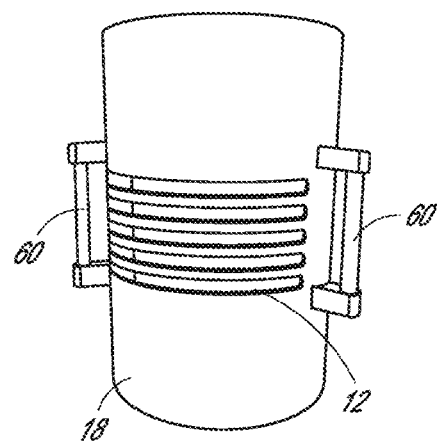
FIG. 12 illustrates a portion of an interface assembly, such as a mask frame or a conduit connector elbow, having a vent and mounting elements, such as mounting posts, configured to engage the mounting elements of the diffuser element of FIG. 11.
Figure 13:
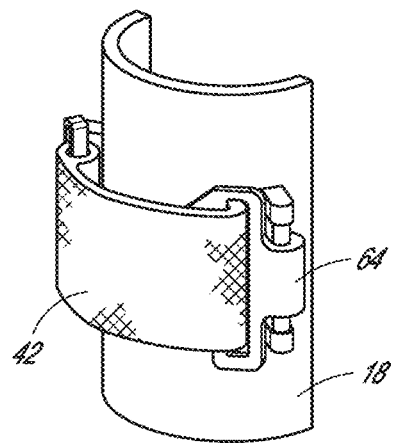
FIG. 13 is a perspective view of the diffuser element of FIG. 11 assembled to the portion of the interface assembly of FIG. 12.

FIGS. 11-13 illustrate another diffuser arrangement comprising a diffuser strap 42 that can be the same as or similar to the diffuser straps 42 of FIGS. 8-10. In the illustrated arrangement, the mounting elements of the mask 14, elbow 18 or other component that defines or carries the vent 12 comprise mounting posts 60 positioned on each side of the vent 12. The diffuser strap 42 includes engagement members configured to engage the mounting posts 60. In the illustrated arrangement, the engagement members of the strap 42 comprise hooks 64 on each end of the diffuser strap 42 configured to engage the mounting posts 60. In some configurations, this arrangement can be reversed and the hooks 64 can be on the mask 14, elbow 18 or other component and the mounting posts 60 can be on the diffuser strap 42. Other suitable mounting elements configured to engage a hook can be used in place of the mounting posts 60.

The hooks 64 can be secured to the diffuser strap 42 by any suitable arrangement, such as those described in connection with FIG. 10 for securing the mounting post 60 to the diffuser strap 42. In some configurations, each end of the diffuser strap 42 comprises a loop that passes through an opening or around a connector bar of the hook 64. The loops of the strap 42 can be created by any suitable process, such as sewing, adhesives or welding, for example. Preferably, the diffuser strap 42 is taut or stretched when applied to facilitate a good seal and to enhance retention.

In an alternative arrangement, opposite ends of the diffuser strap 42 can be connected to one another in a manner similar to that shown in FIG. 10. In some configurations, one end of the diffuser strap 42 can comprise a hook 64 and the other end can comprise a post 60 (or any other combination of selectively coupleable structures) and the diffuser strap 42 can be wrapped around the elbow 18 or other tubular component (e.g., conduit).

Figure 14:
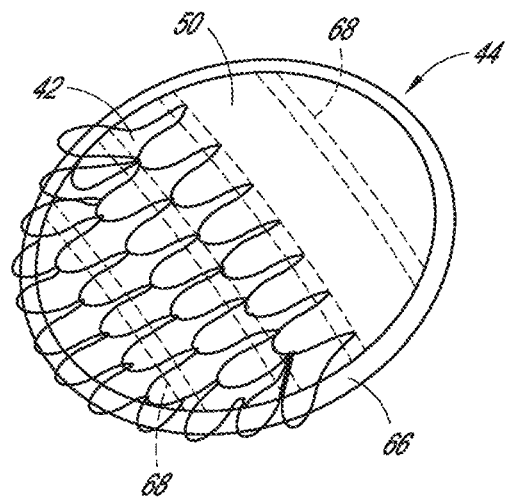
FIG. 14 is a perspective view of a diffuser arrangement comprising a woven or knitted diffuser element applied to a substrate, such as a frame clip.

FIG. 14 illustrates a diffuser arrangement in which the diffuser element 42 is knitted, woven or otherwise intertwined with the support structure 44. Thus, in some configurations, at least a portion of the strands or threads of the diffuser element 42 wrap around a portion of the support structure 44. The wrapping of the strands or threads around the support structure 44 can attach the diffuser element 42 to the support structure such that, in at least some configurations, no additional attachment structures are necessary.

In the illustrated arrangement, the support structure 44 is in the form of a support frame, which includes a perimeter portion 66 and one or more interior support portions 68 that extend from one location on the perimeter portion 66 to another location on the perimeter portion 66. In some configurations, the interior supports 68 are linear struts that extend from one side of the perimeter 66 to the other side of the perimeter 66. The perimeter 66 and the interior supports 68 can be relatively thin such that the support frame 44 defines a number of openings 50 through which exhaust gases can flow. In the illustrated arrangement, the support frame 44 is generally oval in outer shape; however, the support frame 44 can be provided in any other suitable shape, which can correspond to the shape of the associated vent 12. The strands or threads of the diffuser element 42 can wrap around any one or any combination of the perimeter 66 and one or more of the interior supports 68.

Figure 15:
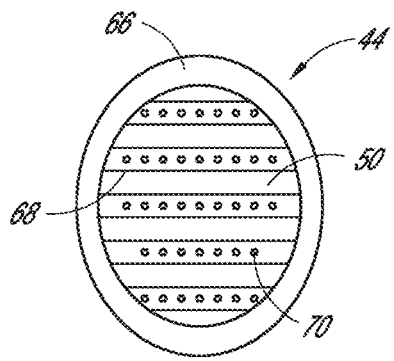
FIG. 15 is a top view of an alternative substrate for a woven or knitted diffuser element that is similar to the substrate of FIG. 14.
Figure 16:
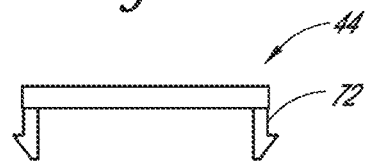
FIG. 16 is a side view of the substrate of FIG. 15.

FIGS. 15 and 16 illustrate a diffuser arrangement similar to the diffuser arrangement of FIG. 14. In the arrangement of FIGS. 15 and 16, the support frame 44 includes a plurality of thread openings 70, which allow one or more strands or threads of the diffuser element 42 to pass therethrough. In the illustrated arrangement, the thread openings 70 are located in the interior supports 68; however, in other configurations the thread openings 70 can be additionally or alternatively located in the perimeter 66. Such an arrangement can assist in maintaining the diffuser element 42 and/or particular strands or threads in place on the support frame 44. For example, the provision of thread openings 70 can assist in inhibiting or preventing migration of strands or threads of the diffuser element 42 in response to a force being applied to the diffuser element 42, such as during cleaning of the diffuser element 42. As illustrated in FIG. 16, the support frame 44 can include coupling elements, such as resilient lock arms 72, which can allow the diffuser arrangement to be coupled to the mask 14, elbow 18 or other component that defines or carries the vent 12.

Figure 17:
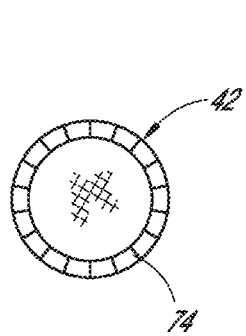
FIG. 17 illustrates a diffuser element having a peripheral mounting cuff.
Figure 18:
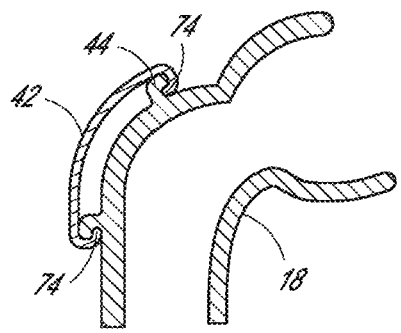
FIG. 18 is a sectional view of the diffuser element of FIG. 17 assembled to a portion of an interface assembly, such as a conduit connector elbow.

FIGS. 17 and 18 illustrate a diffuser arrangement in which the diffuser element 42 comprises a peripheral attachment portion. In the illustrated arrangement, the diffuser element 42 includes a peripheral fold or cuff 74 that permits the diffuser element 42 to be assembled to the mask 14, elbow 18 or other component that defines or carries the vent 12. The diffuser element 42 can be elastic or stretchable such that the cuff 74 can be stretched over the support structure 44 of the mask 14, elbow 18 or other component. In some configurations, the cuff 74 can be stiffened, ribbed or relatively more rigid than other portions of the diffuser element 42 to assist retention of the diffuser element 42 on the mask 14, elbow 18 or other component. In some configurations, the diffuser element 42 can comprise a grip tab, tail or other grasping structure that enables a user to grasp and stretch the diffuser element 42 to assist in assembly or removal.

In the illustrated arrangement, the support structure 44 is in the form of a rim that surrounds the vent 12. The rim 44 can be unitary with or otherwise attached to the mask 14, elbow 18 or other component that defines or carries the vent 12. The rim 44 can be continuous or intermittent around the vent 12. The rim 44 can be of any suitable shape. In some configurations, the rim 44 includes an outwardly-extending flange portion such that at least a portion of the cuff 74 can be positioned underneath the flange portion of the rim 44. Such an arrangement can improve retention of the diffuser element 42 and/or reduce leakage between the diffuser element 42 and the mask 14, elbow 18 or other component that defines or carries the vent 12.

FIG. 19 illustrates another diffuser arrangement that is similar to the diffuser arrangement of FIGS. 17 and 18. The diffuser element 42 of FIG. 19 includes a peripheral attachment portion 74 in the form of a mechanical fastener, such as one portion (e.g., a loop portion) of a hook-and-loop fastener. The mask 14, elbow 18 or other component that defines or carries the vent 12 can include the other portion (e.g., a hook portion) of the hook-and-loop fastener. In some configurations, the strands or threads of the diffuser element 42 serve as the loop portion of the hook-and-loop fastener. In other configurations, an additional loop fastener component is attached to the diffuser element 42. The portion of the hook-and-loop fastener on the mask 14, elbow 18 or other component that defines or carries the vent 12 can be formed or attached in any suitable manner, such as over-molding, welding or adhesion, for example and without limitation.

Similar to the diffuser arrangement of FIGS. 17 and 18, the peripheral attachment portion 74 of the diffuser arrangement of FIG. 19 can surround the vent 12 and can be continuous or intermittent.

FIGS. 20 and 21 illustrate diffuser elements 42 in a generally tubular or sleeve form. Such diffuser elements 42 can be placed over a vent 12 that is defined or carried by a generally tubular structure, such as a portion of a conduit connector elbow 18 or a conduit. For example, such an arrangement is illustrated in FIG. 10. FIG. 20 illustrates a full tube diffuser element 42. The full tube diffuser element 42 defines a diffuser wall portion around at least a substantial portion or an entirety of its circumference. The full tube diffuser element 42 can be formed by circular knitting and can comprise a length of generally constant diameter fabric. The diffuser element 42 can be elastic to facilitate retention and sealing. Such an arrangement can be quick and cost-efficient to manufacture. Such an arrangement also allows the diffuser element 42 to be rotated to move a clean region over top of the vent 12, thus prolonging use between cleaning or disposal of the diffuser element.

FIG. 21 illustrates a partial tube diffuser element 42 that comprises an opening or window 76 that extends around a portion of the circumference of the diffuser element 42. With such an arrangement, the diffuser element 42 can better conform to irregular or non-linear shapes of the mask 14, elbow 18 or other component that defines or carries the vent 12 at least because less material is provided outside of the diffuser portion that covers the vent 12, which can result in less bunching of material. The diffuser element 42 can be elastic to facilitate retention and sealing.

Figure 22:
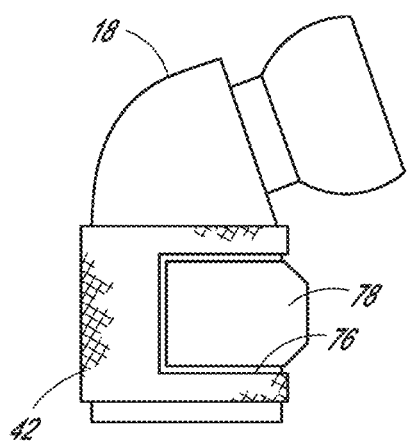
FIG. 22 is a side view of the diffuser element of FIG. 21 assembled to a conduit connector elbow having an alignment feature that facilitates proper alignment and/or retention of the diffuser element.
Figure 23:
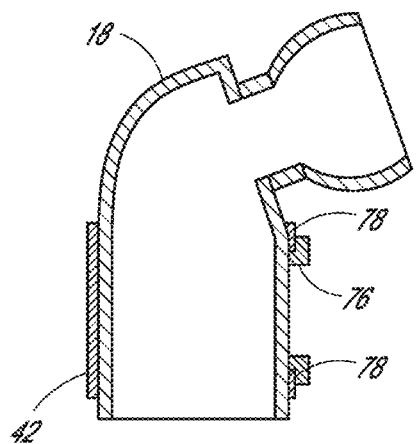
FIG. 23 is a side view of an elbow and diffuser element similar to the arrangement of FIG. 22 with an alternative alignment feature.

With further reference to FIGS. 22 and 23, the window 76 of the partial tube diffuser element 42 can be useful for engaging an alignment feature or features 78 provided on the mask 14, elbow 18 or other component that defines or carries the vent 12. In the illustrated arrangement of FIG. 22, the vent 12 is defined by an elbow 18, which includes a single alignment feature 78 that occupies a substantial portion or an entirety of the window 76 of the diffuser element 42. In some configurations, the alignment feature 78 is a semi-cylindrical protrusion that extends around a portion of the circumference of the elbow 18. In other configurations, the alignment feature 78 can take on other shapes or constructions. However, preferably, the alignment feature 78 contacts the diffuser element 42 at an upper portion, a lower portion and portions of the each side of the window 76 to inhibit or prevent rotation of the diffuser element 42 during normal use.

FIG. 23 illustrates an arrangement in which the alignment feature 78 is in the form of one or more hooks or hook-shaped structures. For example, the alignment feature 78 can comprise a plurality of hooks that contact portions of the diffuser element 42 surrounding the window 76. Preferably, the hooks collectively contact the diffuser element 42 at each of the upper, lower and both sides of the window 76. In other configurations, the alignment feature 78 can comprise a single, generally annular rib or flange, which, in at least some embodiments, can define a hook shape in cross-section.

Figure 24:
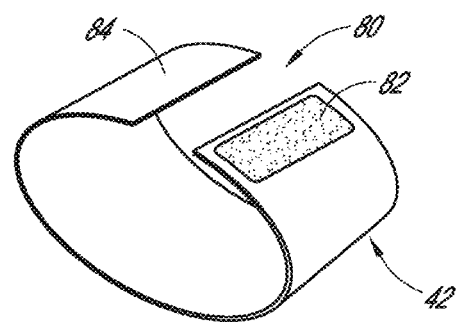
FIG. 24 is a perspective view of an interrupted tube or sleeve type diffuser element having a fastener arrangement that allows end portions of the diffuser element to be selectively connected. The illustrated fastener arrangement is a hook and loop fastener.

FIG. 24 illustrates an interrupted tubular or sleeve diffuser element 42 that is similar to the diffuser element 42 of FIG. 10. The diffuser element 42 can be wrapped around a generally tubular structure that defines or carries the vent 12, such as an elbow 18 or conduit, for example. The opposing ends of the diffuser element 42 can be configured to be secured to one another by any suitable fastener or coupler. Such an arrangement allows the diffuser element 42 to be relatively inelastic because it does not need to stretch for purposes of assembly or removal. In the illustrated arrangement, the ends of the diffuser element 42 are selectively coupled to one another by a hook-and-loop fastener 80. In particular, a hook portion 82 of the hook-and-loop fastener 80 can be secured at one end of the diffuser element 42 and a loop portion 84 can be secured or otherwise provided at the other end of the diffuser element 42. In some configurations, the loop portion 84 is defined by a portion of the material that defines the diffuser element 42, such as the woven or knitted material. The hook portion 82 can be secured to the diffuser element 42 by any suitable arrangement, such as adhesion, sewing, or an ultrasonic, RF or other welding process, for example and without limitation.

Figure 25:
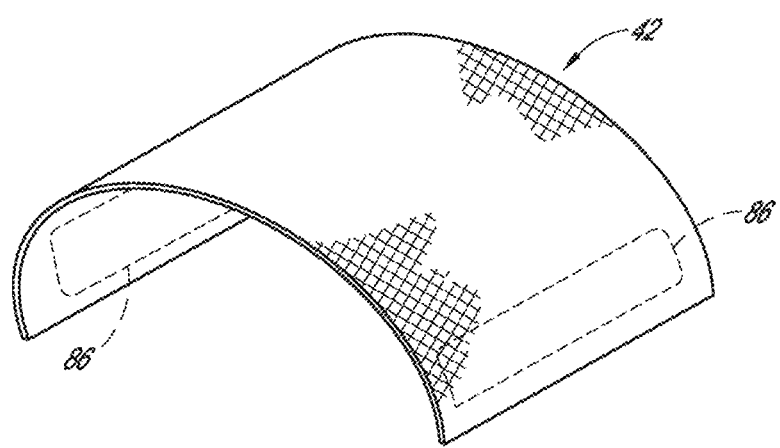
FIG. 25 is a perspective view of an interrupted tube or sleeve type diffuser element similar to the diffuser element of FIG. 24 with a magnetic fastener.

FIG. 25 illustrates an interrupted tubular or sleeve diffuser element 42 similar to that of FIG. 24. However, the diffuser element 42 of FIG. 25 incorporates a magnetic coupler for connecting the ends of the diffuser element 42. In particular, each end of the diffuser element 42 can include a magnetic element 86. The magnetic elements 86 can cooperate to become coupled to one another when the magnetic elements 86 are brought into proximity with one another. Preferably, the magnetic attraction force between the magnetic elements 86 is sufficient to retain the diffuser element 42 in place during normal use, but allows a user to separate the magnetic elements 86 relatively easily by hand for removal of the diffuser element 42. Each magnetic element 86 can be a magnet, or one element 86 can be a magnet and the other element 86 can be a ferromagnetic material component. The magnetic elements 86 can be positioned within internal pockets of the diffuser element 42, such as during or after the process of creating (e.g., knitting or weaving) the diffuser element 42. In some configurations, the interrupted tubular or sleeve diffuser element 42 is magnetically coupled to a mask body of a mask 10, a conduit connector elbow 18 or another component or structure that defines or carries the vent 1, wherein the other structure or component includes a magnet or ferromagnetic material.

In some configurations, the diffuser element 42 is relatively inelastic. However, each of the diffuser elements 42 of FIGS. 24 and 25 can be elastic, if desired. Such an arrangement can assist in maintaining the diffuser element 42 in place on the mask 14, elbow 18 or other component that defines or carries the vent 12. In addition, each of the diffuser elements 42 of FIGS. 24 and 25 can include one or more openings or windows (such as window 76 shown in FIG. 21) that can facilitate engagement with an alignment feature 78 or other retention structure, for example.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A diffuser arrangement for diffusing gases exhausted from a vent of a respiratory interface assembly, comprising:
   a diffuser having a body,
   wherein an entirety of the body is flexible such that the body of the diffuser is configured to conform to a shape of a structure that defines or carries the vent,
   wherein the body is a sleeve that is sized and shaped to cover the vent,
   wherein the sleeve comprises a window configured to engage an alignment feature of the structure that defines or carries the vent,
   wherein the window extends around at least half of a circumference of the sleeve.

2. The diffuser arrangement of claim 1, further comprising the structure that defines or carries the vent, wherein the structure that defines or carries the vent is an elbow or other tubular member, and wherein the body of the diffuser surrounds the elbow or other tubular member.

3. The diffuser arrangement of claim 1, wherein the sleeve comprises at least a portion that is uninterrupted in a circumferential direction.

4. The diffuser arrangement of claim 1, further comprising the structure that defines or carries the vent, wherein the alignment feature of the structure comprises a projection that extends in a circumferential direction.

5. The diffuser arrangement of claim 1, further comprising the structure that defines or carries the vent, wherein the alignment feature of the structure comprises one or more hooks.

6. The diffuser arrangement of claim 1, wherein the body of the diffuser is elastic.

7. The diffuser arrangement of claim 1, wherein the body of the diffuser has at least a portion formed from a knit or woven material.

8. The diffuser arrangement of claim 1, wherein the alignment feature of the structure occupies an entirety of the window of the sleeve.

9. The diffuser arrangement of claim 1, wherein the alignment feature comprises a semi-cylindrical protrusion, an annular rib, or a flange.

10. A diffuser arrangement of claim 1, further comprising the structure that defines or carries the vent, wherein the alignment feature is diametrically opposed from the vent.

11. A respiratory interface comprising the diffuser arrangement of claim 1, wherein the respiratory interface comprises a seal member, wherein the alignment feature of the diffuser arrangement is separate from the seal member, wherein the diffuser is located away from the seal member.

* * * * *